United States Patent [19]

Glassman

[11] Patent Number: 4,810,247
[45] Date of Patent: Mar. 7, 1989

[54] URINARY CATHETER AND PENILE-CUP

[76] Inventor: Jacob A. Glassman, 1680 Michigan Ave., Miami Beach, Fla. 33139

[21] Appl. No.: 88,775

[22] Filed: Aug. 24, 1987

Related U.S. Application Data

[63] Continuation of Ser. No. 800,187, Nov. 21, 1985, abandoned, which is a continuation-in-part of Ser. No. 508,569, Jun. 28, 1983, abandoned.

[51] Int. Cl.⁴ .............................................. A61M 5/00
[52] U.S. Cl. ..................................... 604/171; 604/174
[58] Field of Search .................................... 604/96–99, 604/171, 172, 174, 265, 280–284, 317, 328, 181, 346–353

[56] References Cited

U.S. PATENT DOCUMENTS

| | | | |
|---|---|---|---|
| 1,661,494 | 3/1928 | Nielson | 604/174 |
| 2,764,975 | 10/1956 | Greenberg | 604/174 |
| 3,353,538 | 11/1967 | Carrigan | 604/352 |
| 3,403,682 | 10/1968 | McPonell | 604/352 |
| 3,631,857 | 1/1972 | Maddison | 604/349 |
| 3,648,700 | 3/1972 | Warner | 604/349 |
| 4,378,018 | 3/1983 | Alexander et al. | 604/350 |
| 4,381,380 | 4/1983 | Le Veen et al. | 604/265 |
| 4,419,097 | 12/1983 | Rowland | 604/174 |

FOREIGN PATENT DOCUMENTS

| | | | |
|---|---|---|---|
| 1558162 | 2/1969 | France | 604/280 |
| 8401721 | 5/1984 | PCT Int'l Appl. | 604/280 |
| 2075847 | 11/1981 | United Kingdom | 604/349 |

*Primary Examiner*—C. Fred Rosenbaum
*Assistant Examiner*—J. L. Kruter
*Attorney, Agent, or Firm*—Elmer L. Zwickel

[57] ABSTRACT

A penile-cup of a character that has an open expanded upper end and an open lower constricted end forming a passageway to receive a penile catheter therethrough. The lower constricted end can be constricted about the catheter to prevent fluid leakage and restrain the catheter from upriding in the urethral canal and into the bladder. The preferred structure includes one or more adhesive coated elements extending from the expanded upper end of the penile-cup to afford securement of the penile-cup to the penile-shaft.

2 Claims, 3 Drawing Sheets

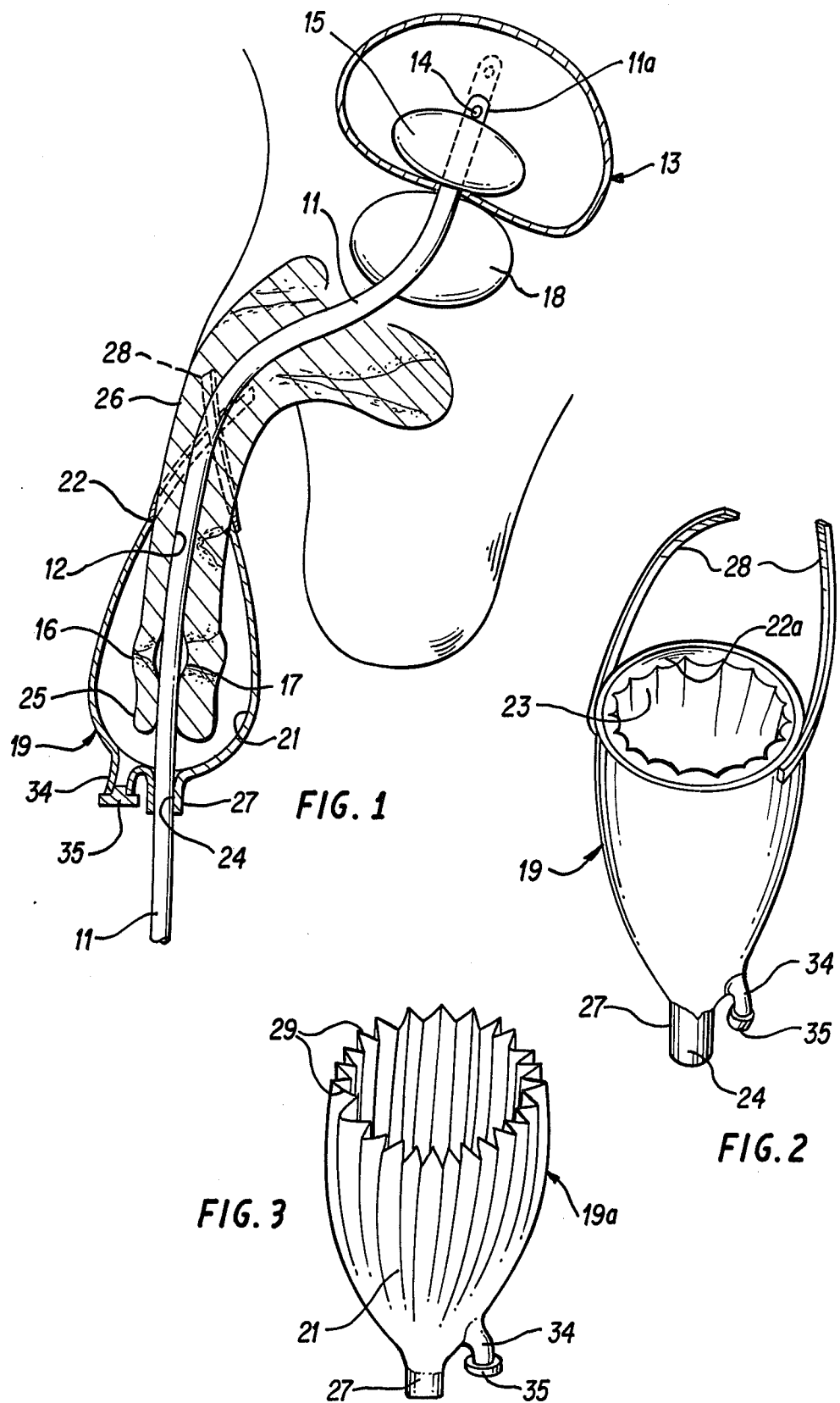

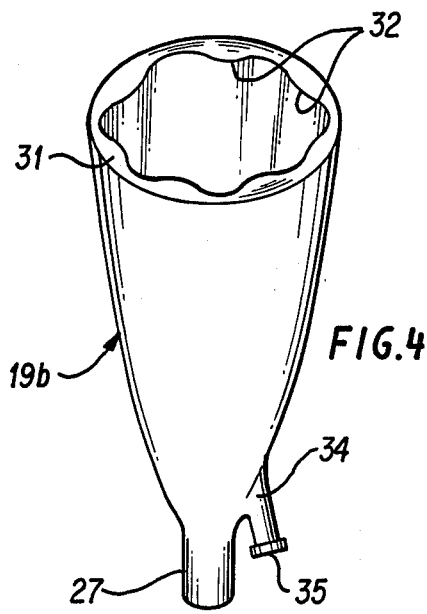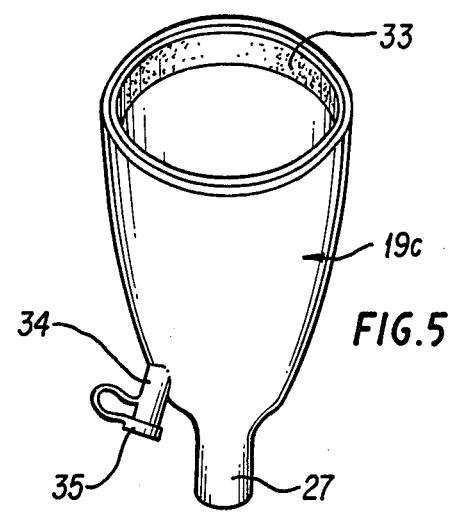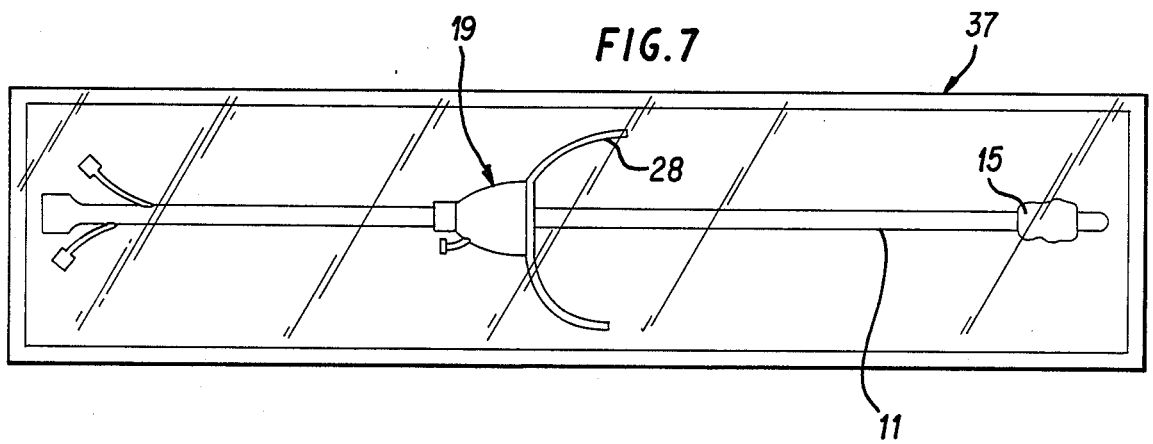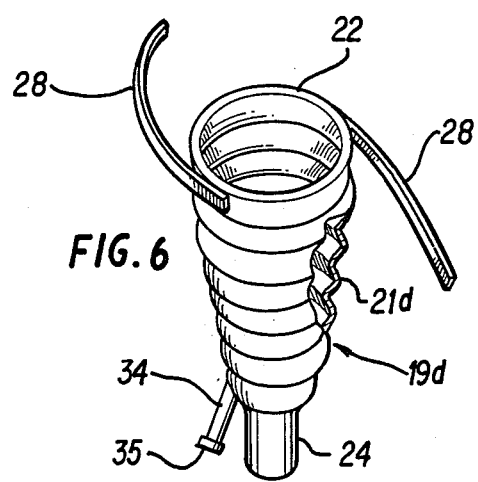

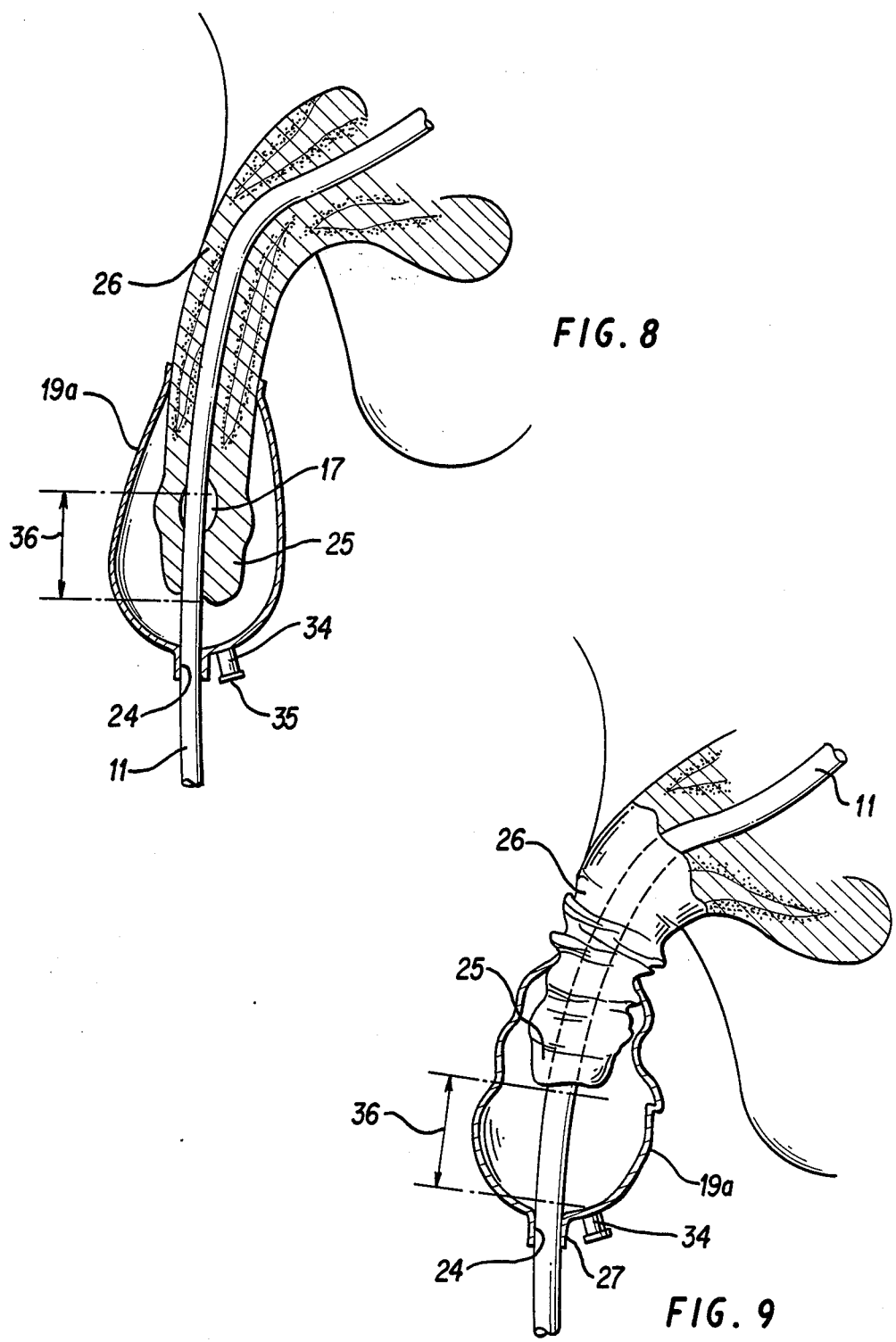

URINARY CATHETER AND PENILE-CUP

This application is a continuation of application Ser. No. 800,187, filed Nov. 21, 1985 for Urinary Catheter and Penile Cup or Sac; which application was a continuation-in-part of application Ser. No. 508,569, filed June 28, 1983, and both now abandoned.

BACKGROUND OF THE INVENTION

The present invention relates to the development of penile-cups for use in conjunction with urethral catheters to minimize post-catheterization infection of the urethral canal, the prostate, and the urinary bladder. It is, at present, common to expect a urethral canal and related parts of the urinary tract to become infected due to contamination of one or more of the following causes:

(a) contamination of hands, gloves and catheter;
(b) faulty preparation of the skin of the penis and/or of the penile urethra;
(c) faulty care of drapes;
(d) contamination of the site of the connection between the catheter and collecting tubing or collector-bags;
(e) during the post-catheterization period when the catheter and connecting tubing is totally ignored. In particular, contamination can and does result from contact of the juncture of the catheter and the penile head with unclean, unsterilized bedding which usually is soiled with urine, feces and other infected secretions.

Still another cause of post-catheterization infection results from irrigating the urinary bladder via the main lumen of the catheter. Specifically, infection results primarily from unwashed or unclean hands, careless manipulating the penile-catheter junction and the catheter.

In fact, without the presence of the herein disclosed cone-shaped cups, which have an imperforate wall extending their entire length, the immediate environment of the penile-catheter junction becomes instantly contaminated and bacterial invasion starts upwardly toward the fossa navicularis in the distal urethra where the bacteria grow and colonize prior to ascending into the upper urethra and into the urinary bladder and kidneys.

In accordance with the present invention, as outlined hereinabove, the said invention is intended to prevent or at least minimize contamination of the catheter and of the penile-urethra by avoiding contact of the penile-catheter areas with unclean hands, bedding, drapes and contaminated catheters and other nearby contaminated objects.

It is therefore an object of this invention to provide means to prevent contamination of the penile-catheter junction of an introduced catheter; of the catheter itself; of the urethral canal and of other critical areas of such installation.

Another object is to provide a cone-shaped penile-cup to prevent contamination by reason of careless handling of the patient and catheter, and because of existing unclean bedding and drapes.

Another object is to provide penile-cups each of which is adapted to be removably anchored to the penile shaft in such manner as to enclose the juncture between the penile-head and the catheter.

Another object of the invention is to provide a transparent cone-shaped penile-cup having means at the smaller of its ends to be fitted snuggly over and be detachably secured to a catheter extending axially through said cone-shaped penile-cup; and means on the penile-cup extending from the larger diameter end for attachment to the penile-shaft to prevent displacement of the penile-cup.

Other advantages and objects of the invention will become apparent with reference to the following description and the accompanying drawings:

IN THE DRAWINGS

FIG. 1 is a schematic view of the penis and related organs, partially in section, illustrating the catheter and its association with a cup, and showing in full lines, the normal positioning of the catheter within the urethral canal while showing, in dotted lines, the approximate position of the distal end of the catheter should it ride up into the bladder.

FIG. 2 is an enlarged perspective of a penile-cup similar to that shown in FIG. 1, with the addition of a liner 23.

FIGS. 3, 4 and 5 are each enlarged perspective views of other modified forms of cups.

FIG. 6 is a similar perspective view of another form of an extensible cup;

FIG. 7 is a plan view of a combination catheter and cup unit, sterilized and sealed in a package for commercial distribution.

FIG. 8 illustrates a penile-cup combination much like that shown in FIG. 1, but is concerned with normal independent shrinkage of the penis and its relationship with the urethral catheter.

FIG. 9 is representative of the penis illustrated in FIG. 8, after it has "shrunk", resulting in exposure of a length of the sterilized catheter outside the penile head.

Referring to the representative disclosures in the accompanying drawings of various embodiments of the invention, wherein like numbers are used to identify similar or related parts, and particularly to FIGS. 1 and 2, which a urethral catheter 11 extending through the penile urethra 12 and into the bladder 13. As shown, the distal end 11a of the catheter, which has an orifice 14 near its end, carries a balloon 15 that is inflated after insertion so as to rest on the bladder floor and prevent urine seepage. During catheter use, and without the improvements disclosed herein, a catheterized patient's normal movements in bed, causes the catheter to ride up in the urethral canal 12 sufficiently to cause a contaminated catheter area located just below the penile-corona 16, to advance into the sterile urethral area of the catheter, to invade, colonize in, and contaminate the fosa navicularis 17 of the urethra.

Contamination of the fossa navicularis travels upwardly in the penile urethra canal 12 and infects the prostate 18 and the urinary bladder 13. It is to avoid such contamination by the otherwise sterile catheter 11 (starting at the meatus of the penis) that the herein disclosed and claimed penilecup 19 becomes essential.

The penile-cups 19 shown in FIGS. 1 and 2, embodies a cup-shaped structure which may be fabricated from any suitable material, preferebly strong light weight, soft, pliable transparent plastic. For convenience and better patient comfort, the upper open rim, or distal end, of the penile-cup 19 may be beveled on the inside upper perimeter 22a, or, as shown in FIG. 2, be lined with foam rubber 23. Such structure would be most beneficial to long standing chronic cases that require prolonged or even permanent catheterization and care. Such cup, irrespective of its exact material structure, will be freely slidable over the catheter 11 before insertion of the catheter into the urethra 12. To this end the cup will have a constrictable end orifice 24 at its primary end 27, adapted to receive any size catheter snugly therethrough. The cup can then be shifted upwardly along the catheter to enclose the penile head 25, the corona 16 and the penile shaft 26. Preferably, the orifice 24 will be formed within the tubular resilient ferrule 27 to insure a stretch fit liquid-tight joining of the penile-cup and catheter 11. The penile-cup 19 may include various means to attach it to the penile-shaft 26, such as a number of adhesive-coated strips 28, each adapted to be attached to the penile-shaft 26 in such manner as to retain the penile-cup in place.

FIG. 3 discloses a modified penile-cup structure wherein numerals heretofore used to identify corresponding parts are re-used. Here the cup 19a may be fabricated from the same grade of anti-bacterial material as the FIG. 2 penile-cup. In this structure, the shell 21 is axially corrugated circumferentially, so that its rim 29 may be collapsed around the penile-shaft, and thereby retained snuggly, yet gently, thereover with or without the aid of mounting strips 28.

In FIG. 4 there is illustrated an extra long penile-cup 19b having a relatively thick wall 31 of soft pliable material. The wall has a corrugated interior surface 32 and is fabricated from shape-retaining elastic-type anti-bacterial plastic that will expand while being drawn up over the corona and then self-contract when in place so as to enclose the corona and shaft and prevent infection. It may be noted that none of the cups herein disclosed, snug up around the penile shaft like a condom.

The FIG. 5 penile-cup 19c is similar to the one shown in FIG. 4, but is fabricated from thinner elastic-like material which may be stretched to its maximum to embrace an engorged penis. When the cup is permitted to collapse, its rim draws up tightly about the penile shaft and is adhered to the penile-shaft by an adhesive coated collar 33. This collar preferably is fabricated, as well as are the strips 28 of FIG. 2, from adhesive paper or plastic or other suitable material, coated or impregnated on its surface with a virtually non-irritating antimicrobial substance capable of effectively destroying skin bacteria on contact. When the adhesive is applied to strips 28 of FIG. 6, and to collar 31, as shown in FIG. 3, the adhesive material will adhere to the skin of the penile-shaft without any additional attachment means and without being irritating to the delicate skin.

The penile-cup 19d shown in FIG. 6, may be structured in the manner of and with the anti-bacterial material of the foregoing cups. However, here the cup 19d has its peripheral wall 21d defined by circumferencial accordian pleats to permit adjustment of the cup axially. This cup, as well as all of these previously discussed herein, may include a drain spout 34 having a removable plug 33 on its end. This drain spout is located close to the lowest point of the cup to allow gravity drainage of irregation fluids that accumulate in cup 19 around catheter 11. The orific for the catheters disclosed herein comprises a stretchable and adaptable collar 27 which may be elongated to insure a snug fit around the catheter. Adhesive coated or tie strips 28 on the cup rim 22 can be used to draw the cup rim snugly about the penile shaft.

The penile-cup representation in FIGS. 8 and 9, is concerned with the fact that when the penile-shaft 26, having a sterilized catheter 11 extending therethrough, "shrinks" longitudinally, the penile head 23 is withdrawn upwardly relative to the sterilized catheter leaving a previously covered segment "36" of the catheter within the cup exposed and unprotected. This segment could become contaminated by contact with finges, bedding, clothing, etc. When the penis shaft returns to its enlarged condition and assumes its normal length, the contaminated catheter portion "36" re-enters the penile urethra carrying with it any contamination and bacterial matter thereon which then travels up the urethral canal and into the prostate and bladder.

More specifically, by-passing FIG. 7 for a moment, the penile shaft 26 shown in FIG. 8 includes a catheter 11 that extends through the penile urethra whereupon the penile head 23 and related portion of the catheter 11 are enclosed in a penile-cup 19a; b; c; d;, all as explained hereinbefore. When the penile-shaft 26 "shrinks" as illustrated in FIG. 9, the penile-head 23 moves upwardly along the catheter without carrying the catheter with it, thus exposing the sterile portion "36" of the catheter which had been enclosed in and protected by the penile-head 25 and shaft 26. However, the penile-cup 19a etc., containing anti-bacterial material, remains over and around the penile-head 25 and catheter 11 juncture during penis "shrinking" and prevents outside exposure of the now unprotected sterile portion 36 of the catheter to outside contamination.

In order to minimize the probability that the catheter-cup combination be subject to careless unsanitary bacterial contamination during application, it may be advisable to manufacture the catheter 11 and cup 19a, etc.; as a single unit, sterilise it and then pack it together in one package 37, transparent or otherwise, as illustrated in FIG. 7. This will assure minimal exposure prior to use, because at the time of unpacking and subsequent catheterization, the medical staff will be as sterile as it can possibly be.

Some of the more promising advantages of the new penile-cup combination are:

The stretchable and adaptable penile-cup holds the selected fixed position of the embraced catheter 11 so effectively that no "riding up" of the catheter into the bladder can take place under normal circumstances. This effective catheter fixation with the stretchable stoma prevents the contaminated external surface of the catheter from being drawn up into the sterile urethra canal, to infect and colonize within the fossa navicularis and thus prevent the inevitable resulting complications; namely—urethritis, prostatitis, cytitis and pyelonephritis. The stretchable outlet 24 in the collar 27 so effectively and snuggly holds the catheter in any disposed fixed position along the catheter, that ointment, even liquid solutions may be contained within the cup without leakage.

Although I have described various embodiments and characteristics of the invention in considerable detail, it will be understood that the description thereof is intended to be illustrative rather than restrictive, as details of the structures may be modified or changed without departing from the spirit or scope of the invention. Accordinaly, I do not desire the device to be restricted to the exact construction shown and described.

I claim:

1. A sanitary covering for a penile-corona and shaft open at its top end and of such size and of sufficient length as to loosely enclose the penile-corona and a substantial portion of the penile-shaft, said penile-cup having a semi-cylindrical bottom wall provided with a restricted opening to receive a urinary catheter tube telescoped therethrough and into the penile-urethra with its distal end extending into the bladder, the conical wall of the penile-cup being pliable and of sufficient diameter to avoid contact with the penile-corona and the penile-shaft, means on the upper open end only of the penile-cup to contract its open end sufficiently to retain the penile-cup in position, and a normally closed drainage opening at the bottom of the penile-cup.

2. The structure recited in claim 1, wherein the means to retain the penile-cup in position comprises at least one adhesive coated strip, one end of which is attached to the penile-cup and its other end to the penile-shaft.

* * * * *